United States Patent [19]
Gerber

[11] 4,375,334
[45] Mar. 1, 1983

[54] NEPHELOMETER

[75] Inventor: Hermann E. Gerber, Reston, Va.

[73] Assignee: The United States of America as represented by the Secretary of the Navy, Washington, D.C.

[21] Appl. No.: 274,958

[22] Filed: Jun. 18, 1981

[51] Int. Cl.³ .............................................. G01N 15/02
[52] U.S. Cl. .................................... 356/336; 356/339; 356/341; 356/343
[58] Field of Search ............... 356/336, 339, 341, 343; 250/564, 565, 574

[56] References Cited
U.S. PATENT DOCUMENTS

| | | | |
|---|---|---|---|
| 2,626,361 | 1/1953 | Martine | 250/564 X |
| 3,563,661 | 2/1971 | Charlson et al. | 356/339 |
| 3,953,127 | 4/1976 | Ahlquist et al. | 356/339 |
| 4,123,665 | 10/1978 | Früngel | 250/565 |

OTHER PUBLICATIONS

Beuttell et al., "Instruments for the Measurement of the Visual Range," *J. Sci. Instru.*, vol. 26, pp. 357-359, Nov. 1949.

Primary Examiner—John K. Corbin
Assistant Examiner—Matthew W. Koren
Attorney, Agent, or Firm—Robert F. Beers; William T. Ellis; Kenneth E. Walden

[57] ABSTRACT

A nephelometer and method for measuring optical quality of a marine atmosphere and particularly characterizing its aerosol particle size distribution, visual range and aerosol optical effects in the visible and infrared. There is provided a housing for entrapping a momentary aerosol sampling, a laser source for providing a narrow collimated beam of radiant energy (usually light) through the sample, and plural spaced-apart cosine sensors facing across the radiant energy illuminated sample, with one reading a slightly greater angle than the other, for receiving aerosol particle scattered light. Integrated outputs from the sensors when compared with laser output intensity as a reference signal provide an indication of aerosol particle size distribution and concentration.

5 Claims, 5 Drawing Figures

NEPHELOMETER

BACKGROUND OF THE INVENTION

Various types of nephelometers exist. One of the best known nephelometers is a type sold commercially by Meterological Research Inc. See U.S. Pat. No. 3,563,661 by Robert J. Charlson, et al., issued Feb. 16, 1971 and U.S. Pat. No. 3,953,127 by Norman C. Ahlquist, et al. issued Apr. 27, 1976 for detailed description and operation. Instruments produced according to these disclosures suffer from truncation errors which make them unsuitable for use in marine atmospheres where large aerosol particles often cause deterioration of the atmosphere's optical quality and exacerbate the truncation error. U.S. Pat. Nos. 3,563,661 and 3,953,127 each disclose a cosine light source and a collimated sensor. U.S. Pat. No. 3,563,661 provides an integrating nephelometer having a housing for containing a sample volume of the atmosphere and a light pulse for illuminating a portion of the sample. One detector receives scattered light from the light pulse and provides an electrical output signal in response thereto. Another detector receives light directly from the light source and provides an electrical output signal defining a reference signal caused by light pulse intensity. These two output signals are compared for an indication of light scattered by aerosol particles in the sample.

SUMMARY OF THE INVENTION

The present invention uses a reciprocal nephelometer technique where, instead of a cosine light source and a collimated sensor, there is employed a collimated light source and plural cosine sensors. The reciprocal technique (i.e., collimated light and cosine sensor) was initially discussed by F. G. Beuttell and A. W. Brewer, "Instruments for the Measurement of the Visual Range", *J. Sci. Instrum.* Vol. 26, November 1949, pp. 357–359, but such has been sparingly used. The reciprocal nephelometers described in the above literature and patents use only one cosine sensor.

The present invention differs from the previous instruments by the use of two or more spaced-apart cosine sensors operated in a specific manner which minimizes truncation errors, provides means for establishing particle size distribution, visual range, and aerosol optical effects to other electromagnetic radiation wavelengths ranging from the visible to the infrared.

OBJECTS OF THE INVENTION

It is therefore an object of the invention to provide an improved integrating nephelometer.

It is another object of the invention to provide an integrating nephelometer employing a collimated laser source and plural spaced-apart cosine detectors.

It is still another object of the invention to provide a nephelometer employing a collimated laser output illuminating an aerosol sample so that scattering (reflections) by the aerosol particles is detected by the cosine sensors, and their responsive electrical outputs are related to the aerosol particle size and distribution and concentration.

It is yet another object of the invention to provide a collimated laser radiation source for illuminating an aerosol sample and plural spaced-apart cosine detectors, one seeing a slightly more acute upstream angular view than the other, whereby light reflected thereto by aerosol particles cause electrical output signals capable of integration for determining aerosol particle size distribution and concentration.

Other objects of the invention will become apparent to one upon attaining an understanding of the invention as described in specification and claimed herein when considered in conjunction with the accompanying drawings.

DETAILED DESCRIPTION OF THE PREFERRED EMBODIMENTS

Figure 1:
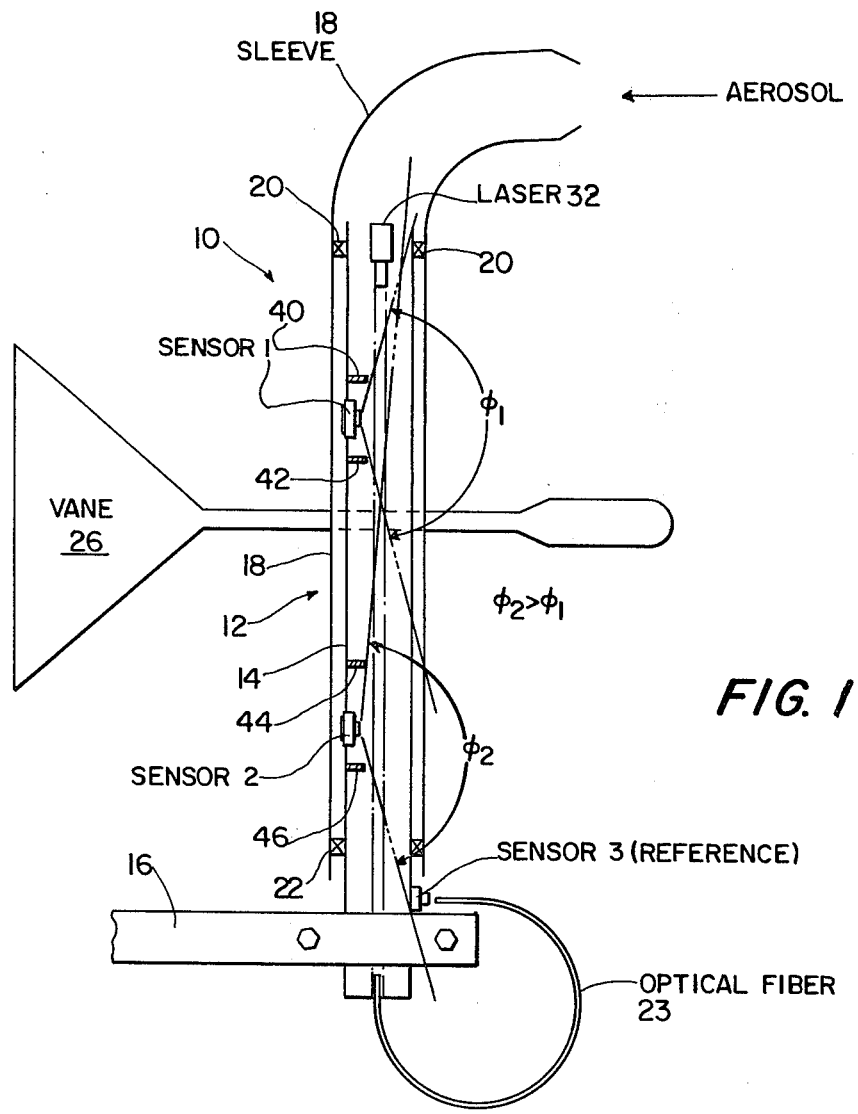
FIG. 1 is a general cross sectional representation of a nephelometer constructed according to the present invention.

A cross sectional view of nephelometer 10 is shown in FIG. 1. Housing 12 includes a tube 14, defining an elongate chamber fixedly secured in an upstanding position from a mounting such as bracket 16, and a sleeve 18, concentrically mounted on the tube by spaced bearings 20 and 22 which allows for pivotal movement. The sleeve is provided with a curved inlet portion which, in use, is kept pointed into the wind by vane 26 for receiving aerosol samplings. It will be understood that the inlet portion may take other shapes and tube 14 may be provided with other arrangements for collecting samplings, such as, for example, when the nephelometer is mounted on an aircraft or other probe and its axis is aligned with the direction of flight.

A GaAs diode laser 32 is mounted in tube 14, as illustrated in FIG. 1, for providing a beam of collimated electromagnetic radiation longitudinally of the tube and through the contained aerosol sampling. The electromagnetic radiation output from the laser may range from the visible to the infrared, but for purposes of this application may be referred to as light. A photoelectric sensor 3 is positioned outside the sampling chamber, such as on tube 14, and coupled with an optical fiber 23, whose end terminates downstream of the laser for monitoring its output intensity. A reference signal provides an indication of laser output. Plural photoelectric sensors 1 and 2, which have precise cosine (Lambertian) responses, are mounted at spaced locations from an internal wall of tube 14. Sensor 2 is located downstream of sensor 1 as shown in FIG. 1. Fences are provided on either side of the sensors for limiting their angular ranges of exposure to light scattered by aerosol particles in the illuminated aerosol sampling. Fences 40 and 42 are mounted inside tube 14 on opposite sides of sensor 1 to limit the sensor's field of view $\phi_1$ from about 13° upstream to about 170° downstream. Fences 44 and 46 are mounted on opposite sides of sensor 2 to limit that sensor's field of view $\phi_2$ to a somewhat larger angle from about 3° upstream to about 170° downstream. Sensor 2 sees a substantial portion of the particles first Mie scattering lobe as well as higher order lobes, whereas sensor 1 sees only the second and higher order lobes. Sensor 2 sees more of the high intensity upstream scattered light. This difference in the field of view permits the outputs of the two sensors to be used to obtain a two-parameter fit to the size distribution of the aerosol particles, with one parameter sensitive to the large particle fraction which is important for marine aerosol detection.

Figure 2:
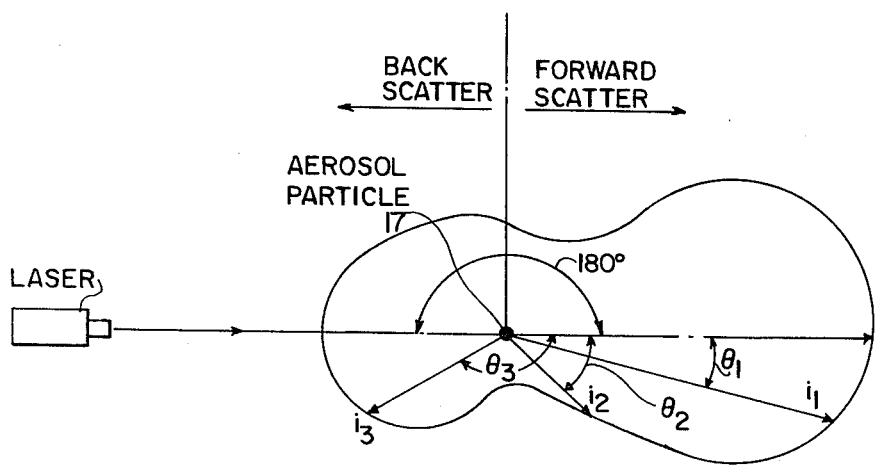
FIG. 2 is a general illustration of electromagnetic radiation scattering intensity.

FIG. 2 is provided for illustrating intensity of scattered light. Radiation, for example, laser light radiation, when passing through a sampling of marine aerosol falls on an aerosol particle 17 and is scattered in intensity according to vectors such as $i_1$, $i_2$, and $i_3$ and at angles of $\theta_1$, $\theta_2$, $\theta_3$ as illustrated. It is known that forward scattered light is brighter (higher intensity) than back scattered light. It is also known that aerosol particle size has an effect on scattering intensity. For example, the larger the aerosol particle size the higher the intensity. It is further known that there is a relationship between light scattering and the wavelength of the light. These known effects and relationships are employed by the present invention for obtaining a more definite determination of aerosol particle size distribution.

Figure 3:
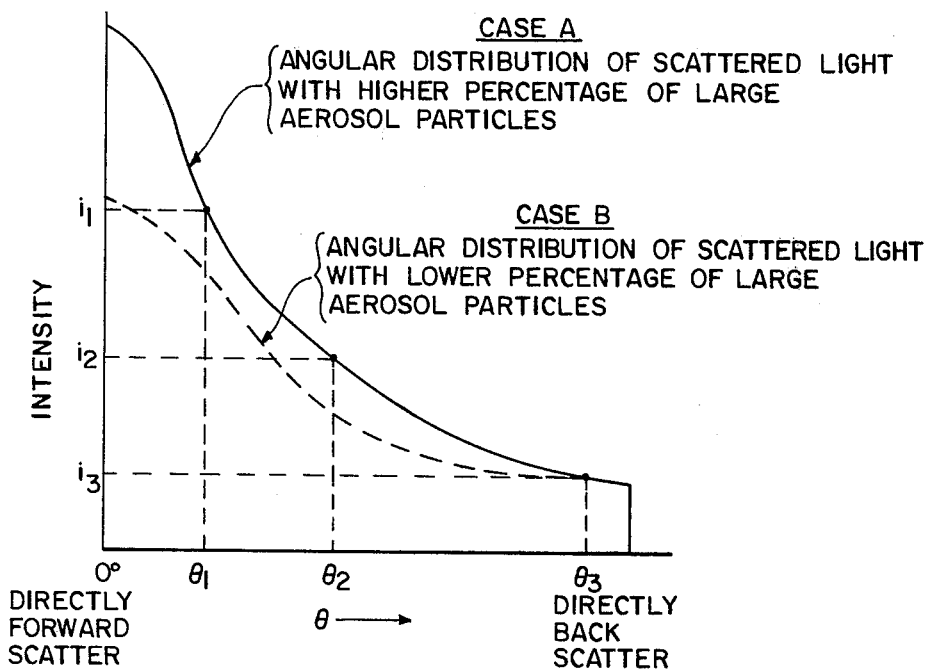
FIG. 3 is a background representation of scattered electroradiation intensity as a function of angle of scatter for both high percentages of large and small aerosol particles.

By way of providing further background, FIG. 3 represents in graph form the light intensity scattered by aerosol particles as a function of scattering angle $\theta$ and the size distribution of the aerosol particles. The angles of $\theta$ has the same meaning as illustrated in FIG. 2. The intensities $i_1$, $i_2$ and $i_3$ of the scattered light in FIG. 3 refer to an ensemble of particles with different sizes.

The shape and magnitude of the curves shown in FIG. 3 vary according to the aerosol particles size distribution as is shown. The curve represented by the solid line (top) is provided as a function of scattering in an aerosol made up of a high percentage of relatively large size aerosol particles, whereas the curve represented by the dashed line (lower) is provided as a function of scattering in an aerosol made up of a high percentage of smaller aerosol particles. As can be seen, the intensities (i) for each function are higher for the forward scattered light than they are for the back scattered light.

Integrating nephelometers with one sensor, which are known in the art, optically integrate the intensities in such curves as shown in FIG. 2 to yield an integrated intensity (I) which is proportional to the aerosol particle scattering coefficient. The integration yields the area under each curve. The known nephelometers when exposed to Case A and Case B will respond to give two different values of I; however, no information on the size distribution of the aerosol particles is contained in those two different values of I.

Figure 4:
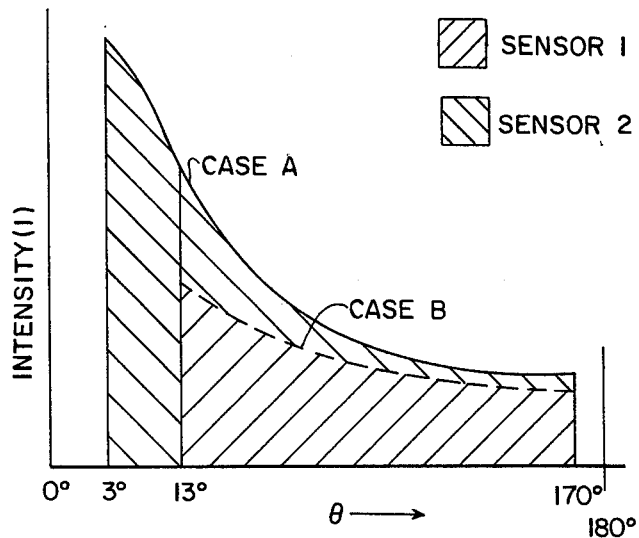
FIG. 4 is a graphical representation of scattered electromagnetic radiation intensity as seen by cosine detectors 1 and 2 of the present invention.

The present invention employs plural spaced-apart photoelectric sensors with cosine responses for providing an indication of size distribution of aerosol particles through the shape of the curves describing the angular distribution of the scattered light intensity. FIG. 4 shows the angular response for the version of the present invention where two cosine sensors are used. Case A and Case B are similar to those described in FIG. 3. As shown in FIG. 4, sensor 1 integrates the scattered light intensities from a scattering angle of 13° to 170°, and sensor 2 integrates the intensities over the larger range of 3° to 170°. The comparison of the integrated intensity $I_1$ from sensor 1 and the integrated intensity $I_2$ from sensor 2 yields information on the size distribution of the aerosol particles, since the shape of the curves of scattered light intensity is dependent on the particle size distribution. The following example shows such a comparison.

EXAMPLE

As illustrated in FIG. 4, Case A represents a reading from an aerosol sampling having a high concentration of a relatively large aerosol particles, and Case B represents a reading from an aerosol sampling having a high concentration of relatively small aerosol particles. Consider the following hypothetical readings wherein the sampling is made up of a high concentration of relatively large particles:

Case A $(I_1/I_2) = 10$ where the numeral 10 represents a value arbitrarily assigned as representing the ratio of the integrated intensities measured by Sensors 1 and 2.

Case B $(I_1/I_2) = 5$ where the numeral 5 represents a value arbitrarily assigned representing the ratio of the integrated intensities measured by Sensors 1 and 2.

The ratio for Case A is larger than the ratio for Case B, indicating that Case A has an aerosol size distribution with larger particles than the size distribution of Case B. In practice, a previously established catalogue of ratios is established to which the measured ratios are compared in order to determine the aerosol size distribution.

The aerosol size distribution thus estimated, is then used to calculate with known formula (1) the visual range, (2) the truncation error correction, which is necessary due to the loss of scattered light intensity in the angular range of 0° to 3° for sensor 2, (3) the scattering, extinction, and absorption coefficients at wavelengths of light other than the wavelength of the laser light, and (4) the angular distribution of the scattered light at those other wavelengths of light.

The intensity outputs of Sensors 1 and 2 are made with reference to the output intensity form Sensor 3 which is coupled through optical fiber 23 for measuring the output intensity of laser 32. By referencing the outputs of sensors 1 and 2 in this manner, the fluctuation of the output intensity of the laser is of no consequence.

ALTERNATE EMBODIMENT

Figure 5:
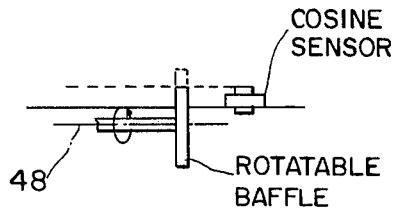
FIG. 5 is a cross sectional representation of a rotatable fence or baffle surrounding a cosine sensor.

The invention has been described so far on the basis of two spaced-apart cosine sensors. One alternate embodiment may include more than two cosine sensors, for example, a row of closely spaced sensors distributed linearly along the inner wall of tube 14. Such an array of sensors provide many I's as identified in the examples. Another alternate embodiment for obtaining many readings may be had by providing the fences on one side of Sensors 1 and/or 2 so that they may be rotated about an axis 48 as illustrated in FIG. 5. As this baffle rotates, its different heights, caused by baffle eccentricity, for example, provide many I's as referred to in the Example. Up to a limit the more I's (either from plural sensors or rotating fences) the better the estimate of sized distribution.

What is claimed and desired to be secured by Letters Patent of the United States is:

1. A nephelometer for monitoring optical quality of a marine atmosphere comprising:
   a housing including an elongate chamber for containing a sampling of marine atmosphere including aerosol particles;
   a laser providing pulses of collimated electromagnetic radiation through the sampling longitudinally of the elongate chamber;
   plural cosine sensors in the chamber longitudinally spaced along the radiated sampling and looking generally transverse to the elongate chamber;
   means admitting scattered radiation to one of the sensors over an angular range from about 170° downstream to about 13° upstream of the radiation, and to the other sensor over an angular range from about 170° downstream to about 3° upstream of the radiation whereby said other sensor receives more forward radiation than the one;
   a third sensor receiving radiation from the laser through the sampling for monitoring laser output intensity and producing a reference signal in response thereto;
   said pair of sensors providing respective output signals in relation to the intensity of scattered radiation received by each over its entire angular ranges; and,
   means comparing the sensor output signals and reference signal;
   thereby providing scattered radiation information.

2. The invention according to claim 1 wherein the means admitting scattered radiation to the sensors is further defined as a fence on either side thereof for admitting more or less upstream scattered light to a sensor.

3. The invention according to claim 2 further defined by the fences adapted to also selectively admit more or less scattered light to respective sensors.

4. The invention according to claims 1 or 2 wherein the means admitting light to the sensors includes a rotatably mounted disc adapted to provide different fence heights upon rotation.

5. The invention according to claim 4 wherein the disc is eccentrically mounted about its rotation axis.